(12) United States Patent
Yamagata et al.

(10) Patent No.: US 9,347,936 B2
(45) Date of Patent: May 24, 2016

(54) INACTIVE CA$^{2+}$/CALMODULIN-DEPENDENT PROTEIN KINASE IIα KNOCKIN ANIMAL AND KNOCKIN CELL OF THE SAME

(75) Inventors: Yoko Yamagata, Okazaki (JP); Yuchio Yanagawa, Maebashi (JP)

(73) Assignee: JAPAN SCIENCE AND TECHNOLOGY AGENCY, Kawaguchi (JP)

(*) Notice: Subject to any disclaimer, the term of this patent is extended or adjusted under 35 U.S.C. 154(b) by 1791 days.

(21) Appl. No.: 10/599,460

(22) PCT Filed: Mar. 24, 2005

(86) PCT No.: PCT/JP2005/005350
§ 371 (c)(1),
(2), (4) Date: Sep. 28, 2006

(87) PCT Pub. No.: WO2005/093051
PCT Pub. Date: Oct. 6, 2005

(65) Prior Publication Data
US 2007/0050858 A1 Mar. 1, 2007

(30) Foreign Application Priority Data

Mar. 29, 2004 (JP) .................. 2004-096995
Dec. 28, 2004 (JP) .................. 2004-380376

(51) Int. Cl.
*A01K 67/027* (2006.01)
*G01N 33/50* (2006.01)
*C12N 9/12* (2006.01)
*C12N 15/85* (2006.01)

(52) U.S. Cl.
CPC ........ *G01N 33/5088* (2013.01); *A01K 67/0276* (2013.01); *C12N 9/1205* (2013.01); *C12N 15/8509* (2013.01); *A01K 2217/072* (2013.01); *A01K 2267/03* (2013.01)

(58) Field of Classification Search
None
See application file for complete search history.

(56) References Cited

U.S. PATENT DOCUMENTS

2007/0050858 A1* 3/2007 Yamagata et al. ............. 800/18

OTHER PUBLICATIONS

Yamagata, Y. et al. "Kinase-Dead Knock0In Mouse Reveals an Essential Role of Kinase Activity of Ca2+/Calmodulin-Dependent Protein Kinase IIalpha in Dendritic Spine Enlargement, Long-Term Potentiation, and Learning", 2009, J. Neurosci., vol. 29: pp. 7607-7618.*
Wang, H. et al., "Inducible protein knockout reveals temporal requirement of CaMKII reactivation for memory consolidation in the brain", Apr. 1, 2003, PNAS, vol. 100: pp. 4287-4292.*
Mak, T. et al., "Knockout mice: a paradigm shift in modern immunology", 2001, Nat. Reviews, vol. 1: pp. 11-19.*
Hedou G and Mansuy IM "Inducible molecular switches for the study of long-term potentiation" Phil. Trans, R. Soc. Lond. B Biol Sci, 358, 797-804, Mar. 14, 2003.
Hanson, PI et al. "Dual role of calmodulin in autophosphorylation of multifunctional CaM kinase may underlie decoding of calcium signals" Neuron, 12, 943-956 (May 1994).
Elgersma Y. et al. "Inhibitory autophosphorylation of CaMKII controls PSD association, plasticity, and learning" neuron, 36, 493-505, (Oct. 24, 2002).
Sutoo D. et al. "Comparison analysis of distributions of tyrosine hydroxylase, calmodulin and calcium/calmodulin-dependent protein kinase II in a triple stained slices of rat brain" Brain Res., 933 (1), 1-11 (Apr. 12, 2002).
Colbran, R.J., "Targeting of calcium/calmodulin-dependent protein kinase II", Biochem J., 378, 1-16 (Feb. 15, 2004).
Mayford, M. et al., Control of memory formation through regulated expression of a CaMKII transgene, Science, AAAS, vol. 274, 1996, pp. 1678-1683.
Giese Karl Peter et al., Autophosphorylation at Thr286 of the alpha calcium-calmodulin kinase II in LTP and learning, Science, vol. 279., No. 5352, 1998, pp. 870-873.
Lisman John et al., The molecular basis of CaMKII function in synaptic and behavioral memory, Nature Reviews Neuroscience, vol. 3, No. 3, 2002, 175-190.
European Search Report, Jun. 1, 2007.

* cited by examiner

*Primary Examiner* — Michael Burkhart
(74) *Attorney, Agent, or Firm* — Wenderoth, Lind & Ponack, LLP

(57) ABSTRACT

The present invention provides an inactive Ca$^{2+}$/calmodulin-dependent protein kinase IIα (CaMKIIα) knockin animal in which only the protein kinase activity of CaMKIIα has been specifically impaired. Since CaMKIIα is considered to be involved in higher brain functions including learning and memory, and inhibit epileptic seizure and brain disorders caused by ischemia, the inactive CaMKIIα knockin animal of the present invention is widely usable for various studies of the brain and nerve, such as the studies of mechanisms of learning disability, dysmnesia, epileptic seizure and brain disorders.

3 Claims, 7 Drawing Sheets

INACTIVE CA²⁺/CALMODULIN-DEPENDENT PROTEIN KINASE IIα KNOCKIN ANIMAL AND KNOCKIN CELL OF THE SAME

This application is the U.S. National Phase under 35 U.S.C. §371 of International Application PCT Patent Application No. PCT/JP2005/005350, filed on Mar. 24, 2005, which claims priority to Japanese Patent Application No. 2004-096995, filed on Mar. 29, 2004, and Japanese Patent Application No. 2004-380376, filed on Dec. 28, 2004, the contents of which are all herein incorporated by this reference in their entireties. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

TECHNICAL FIELD

The present invention is directed to inactive $Ca^{2+}$/calmodulin-dependent protein kinase IIα (CaMKIIα) knockin animals and knockin cells of the same.

BACKGROUND ART $Ca^{2+}$/calmodulin-dependent protein kinase II (CaMKII) is present abundantly in the central nervous system. CaMKII is deeply involved in the control of neuronal activity and the synaptic plasticity by serving as a protein kinase that phosphorylates various proteins and thereby modifies the functions of the proteins. Furthermore, CaMKII is considered to play an important role in higher brain functions including learning and memory, inhibition of epileptic seizure, and inhibition of brain disorder that may be caused by cerebral ischemia (see "PROTEIN, NUCLEIC ACID, AND ENZYME", Vol. 47, No. 1: 51-57, 2002).

CaMKII present in the central nervous system has a multimeric structure whose component is an alpha subunit (CaMKIIα) and a beta subunit (CaMKIIβ). These subunits are highly homologous to each other. Each subunit has the protein kinase activity, the $Ca^{2+}$/calmodulin-binding ability, and the capacity of association between subunits. The α subunit is expressed abundantly in the forebrain, while the β subunit is expressed abundantly in the cerebellum. It is therefore considered that the α subunit is mainly responsible for the above-mentioned CaMKII function.

Until now, simple knockout mice that have lost CaMKIIα protein itself have been produced. Behavior disorders having a relationship with memory and learning, and electrophysiological disorders have been found in these mice. Furthermore, the findings of vulnerability to both convulsion and cerebral ischemia have been also reported (see Science, Vol. 257: 201-206 and 206-211, 1992; Proc. Natl. Acad. Sci. USA, Vol. 92: 6852-6855, 1995; and J. Cereb. Blood Flow Metab., Vol. 16: 1-6, 1996). However, simple knockout mice have lost all of the following three functions: (1) a function as a protein kinase that phosphorylates proteins; (2) a function of binding to calmodulin that is a $Ca^{2+}$-binding protein; and (3) a function of working as a structural protein through binding between CaMKII subunits or binding to other proteins. Thus, it was unclear which loss of function among these functions (1) to (3) was responsible for the various disorders found in the knockout mice. On the other hand, experiments using cultured neurons and brain slices suggest that the function (1) as a protein kinase is more important.

Hence, in order to elucidate the pathology of neuropsychiatric diseases and the molecular mechanisms of brain functions, it is necessary to produce and analyze a specific loss-of-functional animal in which the function (1) alone is specifically lost (so as to say, a "functionally knockout animal"), to distinguishably study the aforementioned functions (1) to (3) of CaMKII.

DISCLOSURE OF INVENTION

The present invention was made in order to overcome the above-mentioned problems, and the object of the present invention is to provide an inactive CaMKIIα knockin animal in which only the protein kinase activity of CaMKIIα has been specifically impaired through the substitution of a CaMKIIα gene into an inactive type, and a knockin cell of the same.

For the above object, the inventors newly produced genetically-modified knockin mice in which an alpha subunit of CaMKII, predominant in the forebrain, has been substituted into an inactive type, using genetic engineering and developmental engineering techniques. The mice thus produced were analyzed and the results led us to the present invention.

That is, the present invention includes the following industrially and medically useful inventions A) to I).

A) An inactive $Ca^{2+}$/calmodulin-dependent protein kinase IIα (CaMKIIα) knockin nonhuman animal, wherein a CaMKIIα gene of one or both of homologous chromosomes is substituted into an inactive type so that an inactive CaMKIIα is expressed. The term "inactive CaMKIIα" used herein means that CaMKIIα is expressed as a protein, and maintains, for example, its calmodulin-binding capacity but its protein kinase activity has been specifically impaired (lost or considerably reduced). The animal may be a heterozygous animal in which one of the homologous chromosomes has been substituted into an inactive CaMKIIα or may be a homozygous animal in which both of the homologous chromosomes have been substituted into an inactive CaMKIIα.

B) The inactive CaMKIIα knockin nonhuman animal according to the above-mentioned paragraph A), wherein the inactive CaMKIIα knockin nonhuman animal is produced by a gene targeting method. As described later, this gene targeting method includes a process of substituting a part of the coding region of the CaMKIIα gene in a genome into another base sequence through homologous recombination for the substitution into an inactive CaMKIIα.

C) The inactive CaMKIIα knockin nonhuman animal according to the above-mentioned paragraph A) or B), wherein one or a plurality of amino acid residues in a catalytic domain of the CaMKIIα has been modified. The term "catalytic domain" denotes a region having protein kinase activity on the N-terminal side of the CaMKIIα and includes an ATP-binding site. Furthermore, the 'modification of amino acid residues' denotes mainly that the amino acid residues are substituted into other amino acid residues, but the meaning thereof includes a wide range of artificial modifications such as deletion, insertion, etc.

D) The inactive CaMKIIα knockin nonhuman animal according to the above-mentioned paragraph C), wherein one or a plurality of amino acid residues that is required for binding to ATP has been modified. The modification of the amino acid residue that is required for binding to ATP allows catalytic activity to be impaired and efficient conversion into an inactive type to be realized.

E) The inactive CaMKIIα knockin nonhuman animal according to the above-mentioned paragraph D), wherein a lysine residue that is required for binding to ATP has been modified. In the case of rat CaMKIIα and mouse CaMKIIα, this lysine residue corresponds to position 42 (in other animals, the position of this lysine may be a little different). For the production of an inactive CaMKIIα knockin mouse as described later, this lysine located at position 42 was substituted into arginine and thus the CaMKIIα was converted into an inactive type. This amino acid substitution can be achieved by introducing a point mutation into a single nucleotide of exon 2 of the CaMKIIα gene.

F) The inactive CaMKIIα knockin nonhuman animal according to any one of the above-mentioned paragraphs A) to E), wherein the inactive CaMKIIα knockin nonhuman animal is a rodent animal.

G) The inactive CaMKIIα knockin nonhuman animal according to the above-mentioned paragraph F), wherein the inactive CaMKIIα knockin nonhuman animal is a mouse.

H) The inactive CaMKIIα knockin nonhuman animal according to the above-mentioned paragraph A), wherein brain's nucleus accumbens has lower neuronal activity as compared to that of a wild type.

I) An inactive $Ca^{2+}$/calmodulin-dependent protein kinase IIα (CaMKIIα) knockin cell, wherein a CaMKIIα gene of one or both of homologous chromosomes is substituted into an inactive type so that an inactive CaMKIIα is expressed. Such an inactive CaMKIIα knockin cell can be also produced by the gene targeting method as described later. It can be also prepared from an animal of the present invention. The inactive CaMKIIα knockin cell may be prepared from a human-derived cell.

Effect of the Invention

In the inactive CaMKIIα knockin animal and knockin cell of the present invention, CaMKIIα is still expressed as a protein. Accordingly, among the above-mentioned functions (1) to (3), the calmodulin-binding capacity described in the above (2), the capacity of multimerizing subunits and the capacity of binding to other proteins (synapse-related proteins including a NMDA glutamate receptor to be described later), that are described in the above (3), are maintained whereas the protein kinase activity alone, described in the above (1), has been specifically impaired.

Thus, the present invention provides a specific loss-of-functional animal (or cell) in which the function (1) alone is specifically impaired, and it is widely usable for brain research including studies of learning disability, dysmnesia, epileptic seizure and brain disorders. For instance, the inactive CaMKIIα knockin animal of the present invention may be useful as a model animal of learning disability, dysmnesia, epileptic seizure and brain disorders. The inactive CaMKIIα knockin animal can contribute to the elucidation of molecular mechanisms thereof and thereby to the progress of brain research.

Furthermore, as described later, the inactive CaMKIIα knockin animal of the present invention is characterized in that the cerebral limbic system thereof such as nucleus accumbens has lower neuronal activity as compared to that of a wild type. It has been known that this brain area regulates emotional behavior. It has been also suggested that this brain area has a relationship with mental diseases including attention deficit hyperactivity disorder (ADHD) and schizophrenia in children. Accordingly, the knockin animal of the present invention may be also useful as a model animal for the research of pathology and therapy of those mental diseases.

Furthermore, the present invention is also useful for screening substrate proteins of the CaMKII.

The further characteristics and advantages of the present invention can be understood fully by the following descriptions. The benefit of the present invention will be made clearer by the following descriptions to be made with reference to the attached drawings.

THE BEST MODE FOR CARRYING OUT THE INVENTION

Figure 1:
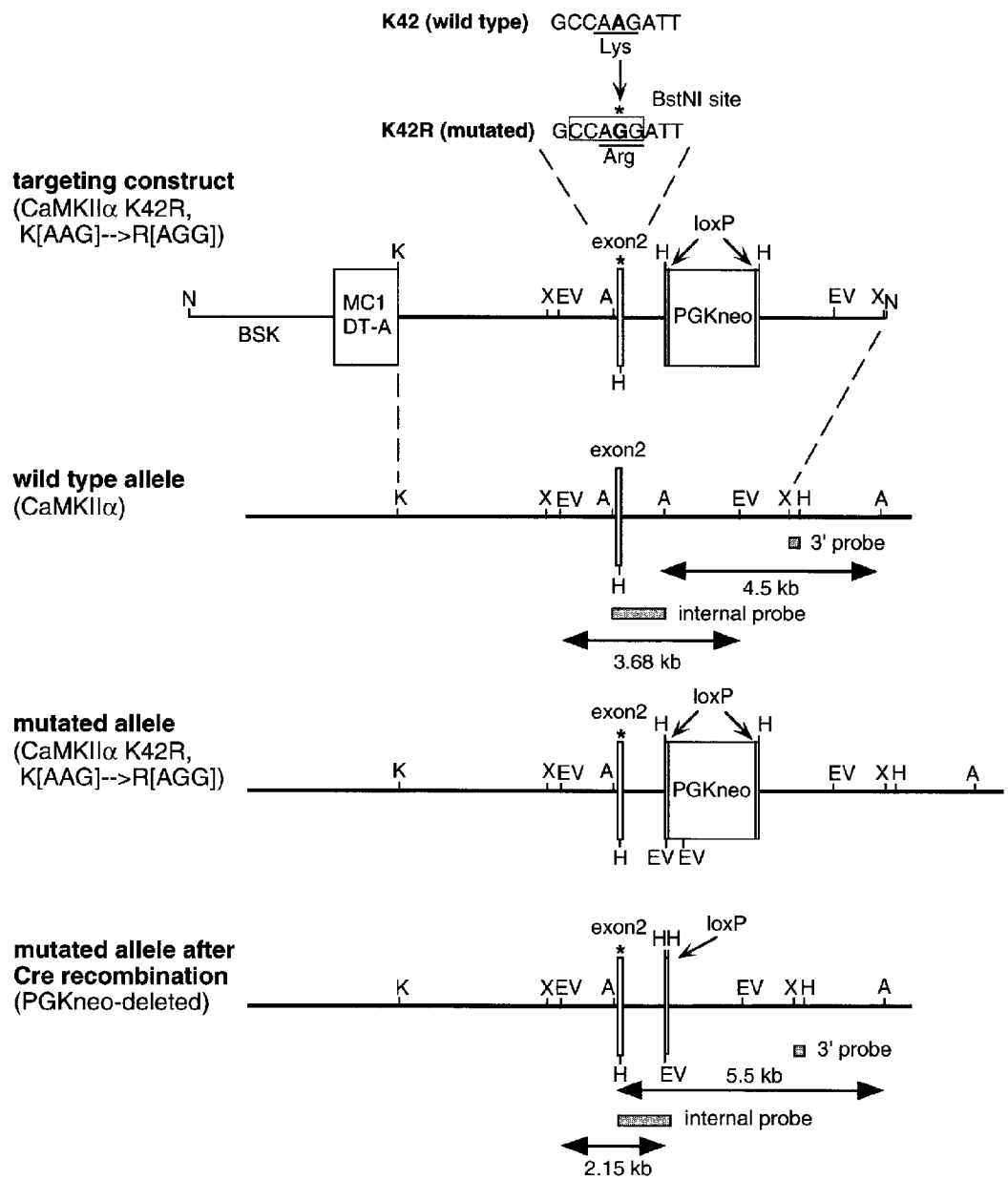
FIG. 1 is a diagram for explaining the gene targeting method used for producing an inactive CaMKIIα knockin mouse according to one example of the present invention.

The inventors produced a knockin animal in which a CaMKIIα gene has been substituted into an inactive type using a gene targeting method as described later in the Examples. Here, a method for producing an inactive CaMKIIα knockin animal using a gene targeting method will be described briefly (details will be described later with reference to the drawings in the Examples).

[1] Preparation of Targeting Vector

First, in order to prepare a targeting vector (a targeting construct), a part of the CaMKIIα gene of a target animal is isolated. For instance, when a knockin mouse is to be produced, a CaMKIIα gene may be screened from a mouse genomic DNA library. The conditions and method of the screening are not particularly limited. The probe to be used for the screening may be prepared from cDNA derived from another animal. In the Examples described later, the mouse genomic DNA library was screened using a probe prepared from cDNA of rat CaMKIIα. Of course, the probe may be prepared from cDNA of mouse CaMKIIα. As alternative, PCR primers may be designed from cDNA or genomic DNA information, and then, for example, a mouse genomic BAC (bacterial artificial chromosome) library may be used for the screening with those primers, so that a part of the CaMKIIα gene may be cloned.

Using a genomic DNA clone obtained through the screening described above, a targeting vector for homologous recombination may be produced. The genomic DNA clone is not required to be the full length of the gene. It is sufficient to clone the region alone that is required for the substitution into an inactive type. In the Examples (of the mouse) described later, the region including exon 2 was subcloned. Then a single nucleotide mutation was introduced to change a base sequence (AAG) into (AGG). The base sequence (AAG) corresponds to the lysine 42 (Lys-42) that is required for the ATP binding. As a result, arginine (Arg-42) was produced and thus the substitution into an inactive type was achieved.

The targeting vector can be prepared by a well-known method. Briefly, it can be prepared by suitably connecting respective fragments of, for example, the genomic DNA clone that has been substituted into an inactive type by the above-mentioned method, a commercially available plasmid, a marker for positive selection (for instance, PGKneo cassette) and a marker for negative selection (a DT-A gene, an HSV-tk gene, etc.). It is advantageous to design the targeting vector so that some restriction enzyme cleavage sites are arranged in suitable positions. Furthermore, the targeting efficiency depends on the length of the homologous region. Accordingly, it is preferable that the homologous region is as long as possible. In addition, a linear targeting vector is preferred to a cyclic one. It is therefore advantageous to arrange a suitable restriction enzyme cleavage site in a region other than the homologous region for the purpose of linearization.

[2] Production of Inactive CaMKIIα Knockin Animal

The targeting vector prepared by the above-mentioned method may be introduced into a totipotent cell derived from a target animal such as an ES cell by, for instance, an electroporation method. Thereafter, the cells in which the intended homologous recombination has occurred are selected. The selection can be efficiently carried out by positive-negative selection. After the selection, the cells in which the intended homologous recombination has occurred are checked by the southern blotting or PCR. Further, in the Examples described later, a neomycin-resistant gene (PGKneo) region for positive selection was removed by Cre recombinase.

A totipotent cell in which the desired homologous recombination has occurred may be introduced into an 8-cell embryo or blastocyst that may be prepared from a pregnant fallopian tube or uterus. The cell may be introduced into such 8-cell embryo or blastocyst by a microinjection method, for example.

The above-mentioned 8-cell embryo or blastocyst may be transplanted into a pseudopregnant animal by a well-known method. A germ-line chimeric animal (preferably, male) born from the animal and a wild-type animal (preferably, female) with homozygous wild-type CaMKIIα genes may be mated with each other. Accordingly, heterozygotes in which the CaMKIIα gene on one of homologous chromosomes has been substituted into an inactive type through homologous recombination can be obtained as the first generation (F1). Furthermore, those heterozygotes may be mated with each other. As a result, homozygotes in which both the CaMKIIα genes on the homologous chromosomes have been substituted into the inactive type can be obtained as the second generation (F2). The heterozygotes and homozygotes may be identified as follows. That is, a part of the body (for example, the tail) is cut, thereafter, DNA is extracted therefrom, and then the genotype is examined by the southern blotting or PCR. Moreover, wild-type animals (homozygotes of wild-type genes) that are littermates of the heterozygotes and homozygotes can be obtained as the second generation (F2). These wild-type animals can be used suitably for control experiments.

The animal to be employed as an inactive CaMKIIα knockin animal is not particularly limited. Examples thereof include mammals such as bovine, pig, sheep, goat, rabbit, dog, cat, guinea pig, hamster, mouse, rat, etc. Among them, rabbit, dog, cat, guinea pig, hamster, mouse and rat are preferable as laboratory animals. Above all, rodent animals are preferable. A mouse is particularly preferable since a number of inbred strains have been produced, and techniques for incubation of fertilized eggs and in vitro fertilization have been developed. Furthermore, the totipotent cell to be used herein can be not only a fertilized egg or an early embryo but also a cultured cell such as a somatic stem cell or an ES cell having multipotency.

The gene targeting method described above is a mere example thereof. It should be appreciated that various well-known modifications can be made. In addition, newly developed methods may be used for production.

For instance, when an inactive CaMKIIα knockin mouse is to be produced, in which the kinase activity alone has been inactivated while the functions based on other functional domains (a calmodulin-binding domain, an association domain) are maintained, it is possible to employ various techniques other than the point mutation of Lys-42 that is required for ATP binding, which was employed in the Examples described later.

From the studies of the kinase domains of various serine/threonine (Ser/Thr) protein kinases, it has been known that the sites required for catalytic activity thereof are composed of the following three functional sites: (1) an ATP-binding site, (2) a catalytic site and (3) a peptide-binding site. A mutation caused in any one of these three functional sites allows the protein kinase activity to be lost and an inactive type to be produced. The inactive knockin mouse of the present invention can be produced by mutation of nucleotide base(s) on exons encoding amino acid residues corresponding to the respective functional sites being targeted, to substitute amino acid(s).

Particularly, methods of converting into an inactive type by chemically modifying the lysine residue (Lys) adjacent to the ATP-binding site or by substituting the lysine residue (Lys) by another amino acid residue such as alanine (Ala), histamine (His), methionine (Met), arginine (Arg), etc. have been tested using various protein kinases. The methods are also employed for confirming the functional importance of kinase activity of a new protein kinase. From the experiment of cDNA expression in cultured cells, it has been confirmed that CaMKIIα is also converted into an inactive type when Lys-42 is substituted by Met, Arg, or Ala (see Neuron, Vol. 12: 943-956, 1994). Accordingly, the Examples described later, adopted the method in which Lys-42, encoded on exon 2, is substituted, as a reliable method.

The inactive CaMKIIα knockin cell of the present invention can be also produced by the gene targeting method described above.

[3] Use (Utility) of the Inactive CaMKIIα Knockin Animal and Knockin Cell of the Present Invention In the inactive CaMKIIα knockin animal and knockin cell of the present invention, the protein kinase activity of CaMKIIα has been specifically suppressed. Of course, they are widely usable for functional analysis of CaMKIIα. However, they are not merely limited to the use for functional analysis of CaMKIIα but have various industrial utilizations (utilities) mentioned below.

(A) Utilization for General Brain Research Including Basic Research and Applied Research As described above, the inactive CaMKIIα knockin animal of the present invention is a "functionally knockout animal" in which the CaMKIIα is expressed as a protein while the protein kinase activity thereof alone has been lost selectively. CaMKIIα is considered to be involved in higher brain functions such as learning and memory and to inhibit epileptic seizure and brain disorders caused by cerebral ischemia.

Accordingly, the inactive CaMKIIα knockin animal of the present invention is widely usable for general brain research including elucidation of the molecular mechanisms of learning disability, dysmnesia, epileptic seizure and brain disorders. For example, it is useful for (1) behavioral/electrophysiological analyses relating to memory and learning, (2) electroencephalographic analyses and experiments for examining spasmophilia using drug administration or intracerebral electrical stimulation, and (3) experiments for examining vulnerability to cerebral ischemia. Furthermore, it may be useful, as a model animal for various brain diseases, for researches of pathology and therapy of various neuropsychiatric diseases as well as researches of the molecular mechanisms of brain functions.

(B) Application to Screening of Substrate Proteins of CaMKIIα

Using an inactive CaMKIIα knockin animal (for instance, a mouse) of the present invention, primary-cultured neurons, brain slices, or the like may be prepared. Then, CaMKII in the cells may be activated by extraneous pharmacological stimuli, followed by phosphorylation proteome analysis. Substrate proteins of CaMKII can be identified comprehensively and effectively, for example, through comparison between a wild-type mouse and a homozygous mouse.

In a knockout mouse in which a CaMKIIα protein itself, which is one of major intracerebral proteins, has been deleted, it is highly possible that expression patterns of other proteins have been varied diversely. Accordingly, the knockout mouse is not suitable for searching substrate proteins. On the other hand, by using an inactive knockin mouse in which the kinase activity alone has been lost while CaMKIIα is expressed as a protein, substrate proteins in the brain can be searched effectively.

(C) Analysis of Effect of Kinase Activity of CaMKIIα on Kinetics of Synaptic Proteins It is possible to examine the kinetics of presynaptic and postsynaptic synapse-related proteins, for example, through comparison between a wild-type mouse and a homozygous mouse, by use of those primary-cultured neurons. This makes it possible to analyze the effect of kinase activity of CaMKIIα on kinetics of synapse-related proteins and synaptic transmission.

The synapse-related proteins are known to show a dynamic kinetic change with neuronal activity. In the presynaptic site, CaMKIIα is involved, as one of synaptic vesicle-binding proteins, in binding of protein such as synapsin I to a synaptic vesicle. On the other hand, in the postsynaptic site, CaMKIIα interacts, as a main component of postsynaptic thickening, with a neurotransmitter receptor or a channel protein. Furthermore, by phosphorylating these synapse-related proteins, the release of the neurotransmitter is regulated and the receptor and channel activities are modified. Accordingly, when using an inactive knockin mouse in which the CaMKIIα activity alone has been lost, which is different from a knockout mouse, the effect of the kinase activity on synaptic transmission and kinetics of the synapse-related protein can be verified effectively without affecting the interaction between proteins.

As described earlier, in the inactive CaMKIIα knockin animal (cell) of the present invention, since CaMKIIα is expressed as a protein, the binding capacity of CaMKIIα to other proteins is maintained. Here, "other proteins" denotes synapse-related proteins, specifically synaptic vesicle-binding proteins, synapsin I, etc. that are present in the presynaptic terminal as well as postsynaptic thickening membrane protein NMDA glutamate receptor, densin-180, etc. that are present in the postsynaptic site.

(D) Analysis of Regulatory Mechanism of Autophosphorylation that Plays Significant Role in CaMKIIα Activity Regulation Using brain homogenates of a wild-type mouse and a homozygous mouse, it is possible to elucidate the in vivo regulatory mechanism of autophosphorylation by comparing and analyzing the autophosphorylation states of CaMKII in the brain.

CaMKII is considered to have an important function for modifying brain functions depending on neuronal activities, as a major member of an intracellular $Ca^{2+}$ signal cascade in the central nervous system. CaMKII is activated by being bound to calmodulin ($Ca^{2+}$-binding calmodulin, $Ca^{2+}$/calmodulin) that has been activated through the rise in intracellular $Ca^{2+}$. As a result, it can phosphorylate various substrate proteins. In this activation, autophosphorylation occurs; that is, autophosphorylation of threonine 286 (Thr-286) (in the case of a rat and a mouse) in a regulatory domain. The autophosphorylation of Thr-286 maintains CaMKII in the activated state, i.e., the protein kinase activity is maintained even after intracellular $Ca^{2+}$ level decreases, unless it is dephosphorylated by phosphatase. Accordingly, the autophosphorylation of Thr-286 is considered to play an important role in synaptic plasticity that serves as a basis of memory and learning, as a switching mechanism that converts the transient rise in intracellular $Ca^{2+}$ into a continuous signal.

CaMKII forms a multimeric structure composed of 10 to 12 homologous subunits (α and β in the brain) (holoenzyme). From various in vitro experiments using purified CaMKII, the autophosphorylation of Thr-286 that is required for activation has been considered to occur between subunits that are adjacent to each other in this holoenzyme. The inactive knockin mouse, in which CaMKIIα is expressed as a protein while the kinase activity thereof alone has been inactivated, allows CaMKIIα to form a multimeric structure by plural CaMKIIα or together with CaMKIIβ. The inactive knockin mouse has CaMKIIα with Thr-286 that serves as a substrate. Accordingly, the inactive knockin mouse may serve as a suitable model for verifying the above-described hypothesis that "the autophosphorylation occurs between adjacent subunits" and for searching whether a new regulatory mechanism exists, by analyzing the autophosphorylation of Thr-286 of CaMKIIα (Thr-287 in CaMKIIβ) in the holoenzyme when the kinase activity thereof is lost. When using a knockout mouse in which the CaMKIIα protein itself has been lost, such analysis is not available.

(E) Utilization as a Model Animal for Searching Therapy and Elucidating Pathology of Neurological Disorders Such as Attention Deficit Hyperactivity Disorder (ADHD)

A histological search was made using the brain of the inactive CaMKIIα knockin homozygous mouse of the present invention produced according to the Examples described later. As a result, no structural abnormalities were observed at optical microscope level. However, according to cytochrome oxidase activity staining that reflects the activity of neurons, the neuronal activity in the cerebral limbic system including nucleus accumbens and amygdala was clearly lower than that of the wild-type mouse (see FIG. 9).

These sites such as nucleus accumbens have been known to control the emotional behavior of an animal through serotonin system and dopamine system. It has been also suggested that they relate to the appearances of mental disorders including schizophrenia and attention deficit hyperactivity disorder (ADHD) in children. Actually, in the above-mentioned knockin mouse, hyperkinetic symptoms are observed from the behavioral point of view. This strongly suggests that the mouse is related to mental disorders with attention deficit.

Hence, the knockin animal of the present invention may be useful as a model animal for searching therapy and elucidating pathology of those disorders and for drug screening.

The inactive CaMKIIα knockin cell of the present invention also has the same utilities as descried in (A) to (E) above.

EXAMPLES

Hereinafter, examples are described in which an inactive CaMKIIα knockin mouse was produced as an inactive CaMKIIα knockin animal of the present invention. However, the present invention is not limited by these examples.

Example 1

Preparation of Targeting Construct

FIG. 1 is a diagram for explaining the gene targeting method used for a method of producing an inactive CaMKIIα knockin mouse of this example. FIG. 1 schematically shows, sequentially from the top, structures of a targeting construct for producing an inactive CaMKIIα knockin mouse, a normal CaMKIIα gene (a wild-type allele), a homologously recombined CaMKIIα mutated gene (a mutated allele), and a CaMKIIα mutated gene in which a neomycin-resistant gene has been deleted by Cre recombinase (a mutated allele after Cre recombination). The letters, N, K, X, EV, A, and H denote restriction enzyme cleavage sites, NotI, KpnI, XbaI, EcoRV, ApaI, and HindIII, respectively.

In this targeting method, first, using cDNA of a rat CaMKIIα that is highly homologous to a mouse, a genomic DNA library of mouse TT2 cell lines (an embryonic stem cell; ES cell) was screened. Thereby a gene fragment containing exon 2 of the mouse CaMKIIα was obtained. The exon 2 is an exon containing base sequences corresponding to lysine 42 (Lys-42) that are at the active center of CaMKIIα. After this gene fragment was inserted into a plasmid vector, a restriction map was produced (see the wild-type allele shown in FIG. 1) and further subcloning was carried out.

By the PCR method using an oligonucleotide with mutation, a single nucleotide mutation was introduced into a base sequence (AAG) corresponding to Lys-42 in exon 2, which caused a point mutation (AGG) so as to encode arginine (Arg-42) (see the targeting construct shown in FIG. 1. In FIG. 1, the asterisk "*" denotes that the point mutation was introduced). This introduction of the point mutation was confirmed by sequencing. This point mutation generated a new cleavage site digested by BstNI restriction enzyme (see FIG. 2).

Furthermore, a neomycin-resistant gene (PGKneo) sandwiched between loxP sequences was inserted into an ApaI restriction enzyme cleavage site in the intron on the 3' side of exon 2, while a diphtheria toxin A gene (MC1-DT-A) was inserted into a nonhomologous region. Thus a targeting construct was prepared (see the targeting construct shown in FIG. 1).

Example 2

Introduction of Targeting Construct into ES Cell

The above-mentioned targeting construct was prepared in bulk and then linearized by a restriction enzyme digestion. This construct was used for electroporation into an ES cell (TT2 cell). Neomycin-resistant ES colonies were picked up through screening that was performed using antibiotic G418 and then the genomic DNAs thereof were analyzed by the PCR method and southern blotting. As a result, four homologous recombinants were identified out of a total of 524 colonies. The structure of the allele with the homologous recombination is shown in the diagram identified as "mutated allele" in FIG. 1.

In the positive colonies obtained by the above-mentioned method, the actual introduction of intended mutation was confirmed by sequencing of the PCR product (the fragment of 0.29 kb shown in FIG. 2) in the region including the point mutation. Into two positive colonies out of them, Cre recombinase was introduced together with puromycin N-acetyltransferase (Pac) by electroporation using expression vectors. Thereafter, ES colonies with the Cre recombinase were picked up through screening that was performed using the antibiotic, puromycin. The genomic DNAs thereof were analyzed by the PCR method and southern blotting. Thus positive colonies were obtained in which the neomycin-resistant gene was deleted by the Cre recombinase and thereby the loxP sequence alone remained (see "mutated allele after Cre recombination" shown in FIG. 1). Similarly, with respect to these positive clones, the actual introduction of intended mutation was confirmed by sequencing of the PCR product in the region including the point mutation.

Example 3

Production of Inactive CaMKIIα Knockin Mouse

The positive clone of the above-mentioned ES cell in which the homologous recombination had occurred and the neomycin-resistant gene had been deleted was microinjected into a mouse 8-cell stage embryo. Thus a chimeric mouse was obtained. Furthermore, this chimeric mouse was mated with a wild-type mouse. As a result, a mouse having genes derived from the ES cell, "an inactive CaMKIIα knockin mouse", was obtained.

Example 4

Analysis of Inactive CaMKIIα Knockin Mouse—Analysis at DNA Level

Figure 3:
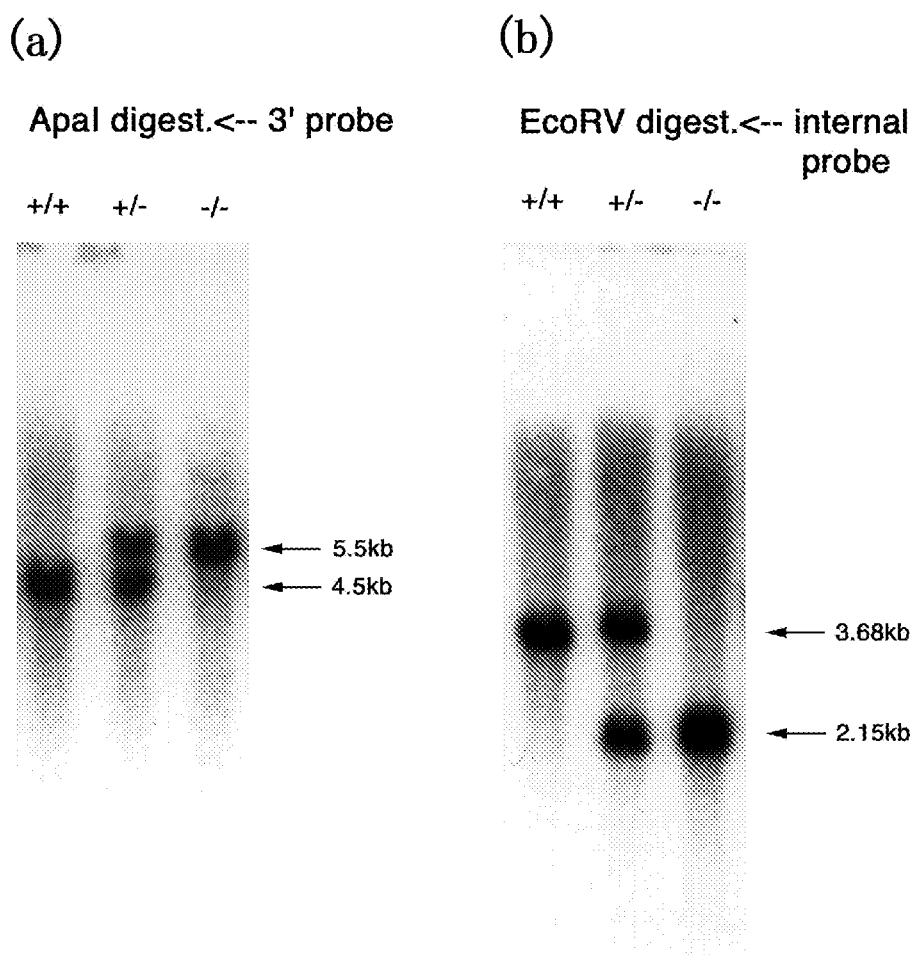
FIGS. 3(a) and (b) are diagrams showing the results of southern blotting of genomic DNAs.

With respect to the inactive CaMKIIα knockin mouse produced by the above-mentioned method, it was checked by southern blotting whether a mutated gene had been introduced through homologous recombination. FIG. 3 shows the experimental results.

Genomic DNAs were extracted from tissues of tails of a wild-type mouse (+/+), a heterozygous mouse (±) in which an inactive CaMKIIα gene had been introduced into one of homologous chromosomes, and a homozygous mouse (−/−) in which an inactive CaMKIIα gene had been introduced into both of homologous chromosomes. Then they were subjected to southern blotting. The probes used herein were the following two types: a 3' probe that corresponds to the nonhomologous region at downstream of the 3' side of the targeting construct, and an internal probe that corresponds to the homologous region within the targeting construct (see FIG. 1). FIG. 3(a) shows the results of detection with the 3' probe after the respective genomic DNAs were digested with a restriction enzyme ApaI. On the other hand, FIG. 3(b) shows the results of detection with the internal probe after they were digested with a restriction enzyme EcoRV.

In the case of the wild-type mouse (+/+), bands of 4.5 kb and 3.68 kb were detected in (a) ApaI digest and (b) EcoRV digest., respectively. On the other hand, in the case of the inactive CaMKIIα knockin mouse (−/−), bands of 5.5 kb and 2.15 kb indicating the homologous recombination were detected in (a) ApaI digest and (b) EcoRV digest., respectively. In the case of the heterozygous mouse (+/−), both the bands that were observed in the wild-type and homozygous mice were detected. From the experimental results shown in FIG. 3, it was confirmed that the mutated gene was introduced by homologous recombination.

Figure 4:
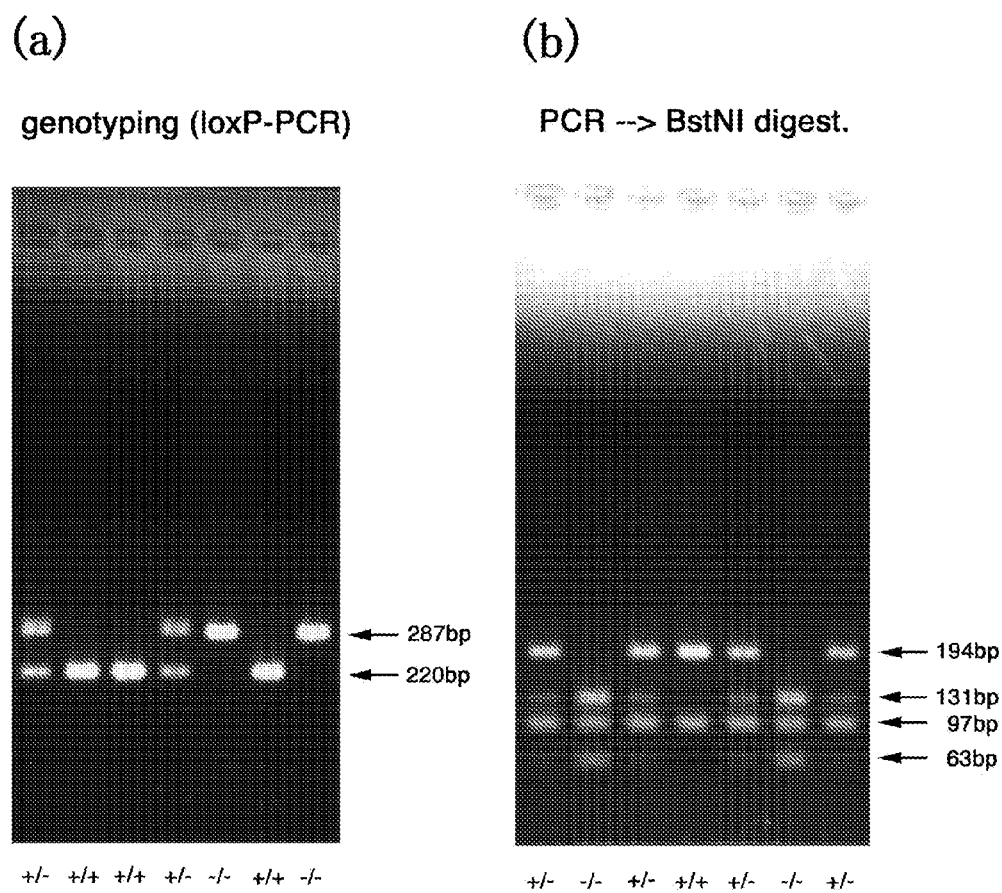
FIGS. 4(a) and (b) are diagrams showing the results of PCR analysis of genomic DNAs.

Furthermore, genotyping of the respective mice was performed by the PCR analysis of genomic DNAs. FIG. 4 shows the results. FIG. 4(a) shows the results of genotyping of respective mice to determine whether the loxP sequence was present by the PCR analysis (loxP-PCR) using primers sandwiching the loxP sequence insertion part. In the inactive type, the loxP sequence remained to be inserted in the intron at the downstream of exon 2. As shown in FIG. 4(a), the loxP-PCR product of the wild-type mouse (+/+) is 220 bp, while that of the homozygous mouse (−/−) is as long as 287 bp due to the insertion of the loxP sequence.

Figure 2:
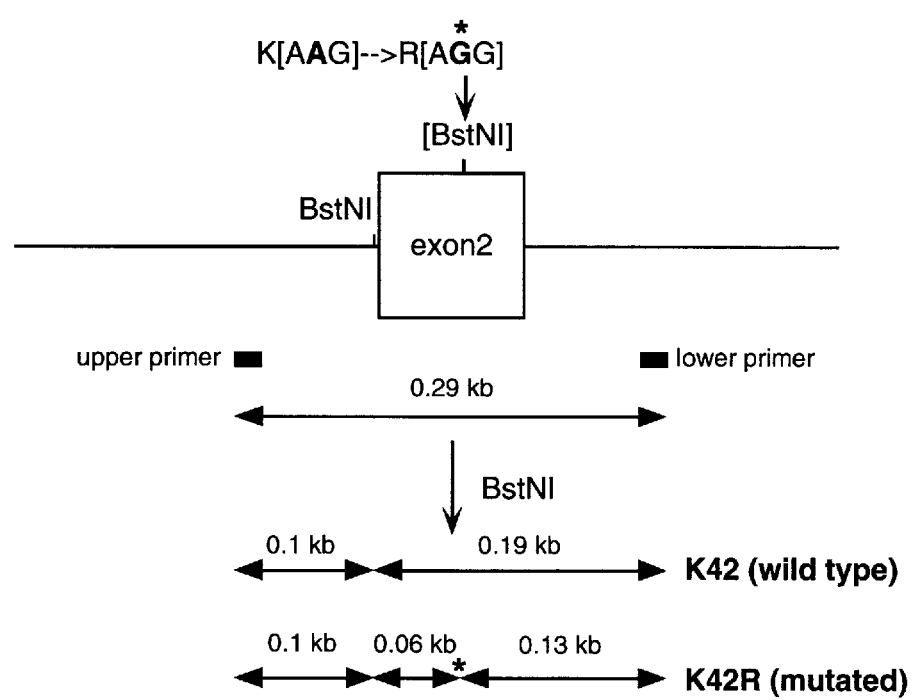
FIG. 2 is a diagram showing that a single nucleotide substitution caused a new BstNI restriction enzyme cleavage site.

FIG. 4(b) shows the results of experiments, in which the PCR product including the point mutation part in exon 2 was digested by the BstNI restriction enzyme (PCR→BstNI digest.) and a new cleavage site was examined to determine whether the substitution (point mutation) occurred. As shown in FIG. 2, a single nucleotide substitution (point mutation) converts the base sequence AAG (corresponding to Lys-42) that is present in exon 2 of the CaMKIIα gene into AGG (corresponding to Arg-42), and thereby a new BstNI restriction enzyme cleavage site appears. Accordingly, as shown in FIG. 4(b), two bands of 194 bp and 97 bp appear in the wild-type mouse (+/+), while three bands of 131 bp, 97 bp, and 63 bp appear in the homozygous mouse (−/−) because of the appearance of the new BstNI restriction enzyme cleavage site. In the heterozygous mouse (+/−), four bands of 194 bp, 131 bp, 97 bp, and 63 bp can be detected.

Figure 5:
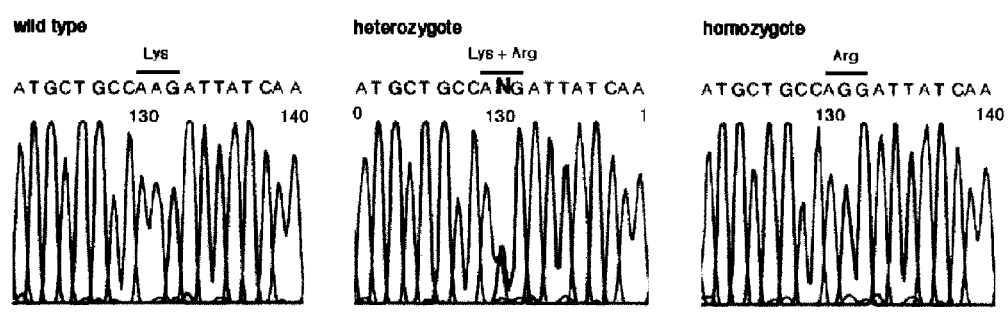
FIG. 5 is a diagram showing the results obtained by directly confirming a point mutation, through sequencing.

Furthermore, the introduction of the point mutation was confirmed by direct sequencing of the PCR product including the point mutation part in exon 2. FIG. 5 shows the results. A base sequence (AAG) corresponding to Lys-42 and a base sequence (AGG) corresponding to Arg-42 were confirmed directly in the wild-type mouse and in the homozygous mouse (homozygote), respectively, while a mixture of AAG and AGG sequences was confirmed directly in the heterozygous mouse (heterozygote).

Example 5

Analysis of Inactive CaMKIIα Knockin Mouse—Analysis at Protein Level

Figure 6:
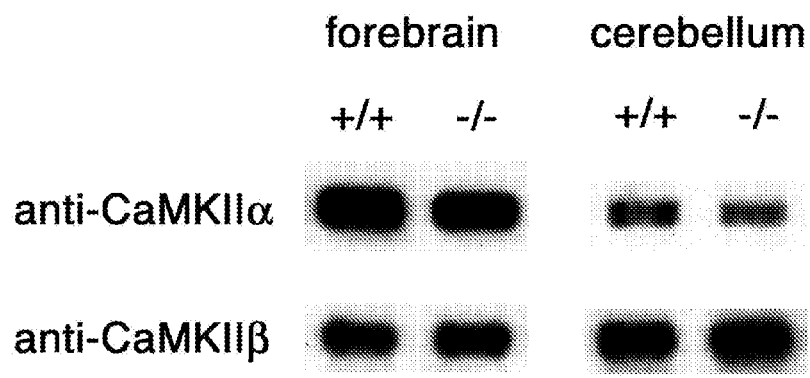
FIG. 6 is a diagram showing the results of analysis of the CaMKII protein expression by Western blotting.

Next, using a mouse brain homogenate, the protein level was analyzed by Western blotting. FIG. 6 shows the results. With an antibody that reacts specifically to CaMKIIα, no clear difference in CaMKIIα protein level between the wild-type mouse (+/+) and the homozygous mouse (−/−) was found in both the forebrain and cerebellum (the upper panel shown in FIG. 6). This suggests that genetic manipulation of a single amino acid substitution hardly affects the level of expression of CaMKIIα protein. Furthermore, another subunit β of CaMKII was also examined using a specific antibody. As a result, no difference in its expression between the wild-type mouse and the homozygous mouse was found in both the forebrain and cerebellum (the lower panel shown in FIG. 6).

Figure 7:
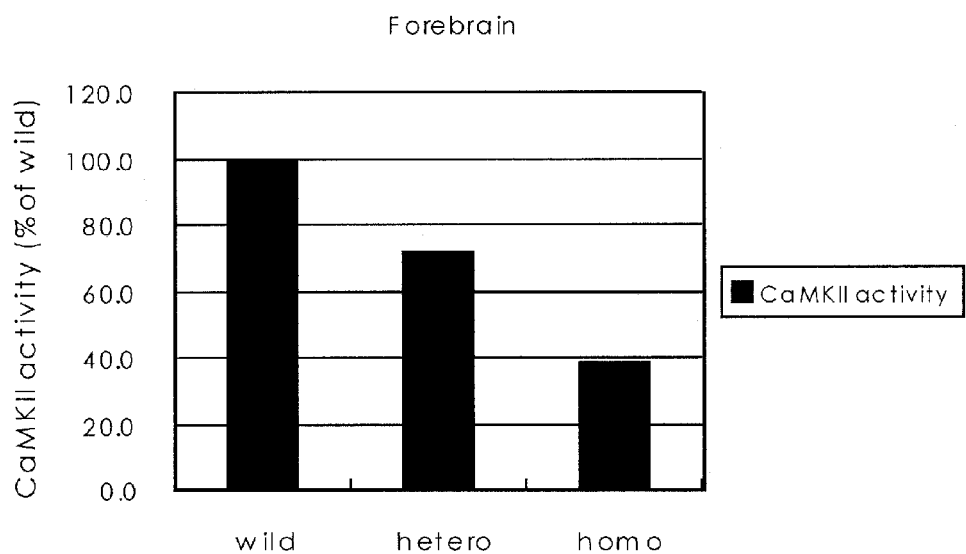
FIG. 7 is a graph showing the results of CaMKII activity measurement in a forebrain homogenate.

Subsequently, using a mouse brain homogenate, the activity of CaMKII was measured with a specific peptide substrate. Consequently, as shown in FIG. 7, in the forebrain where CaMKIIα is predominant as compared to CaMKIIβ, the activities found in the heterozygous mouse (hetero) and the homozygous mouse (homo) were merely 71.5% (about 70%) and 38.8% (about 40%) of that of the wild-type mouse (wild), respectively. The remaining activity in the homozygous mouse is considered to be attributed to CaMKIIβ.

Figure 8:
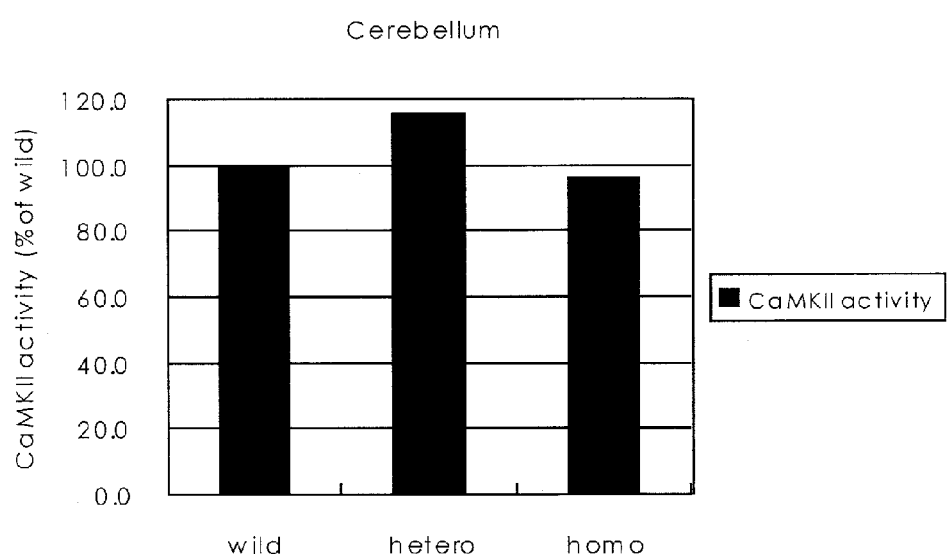
FIG. 8 is a graph showing the results of CaMKII activity measurement in a cerebellum homogenate.

On the other hand, in the cerebellum where CaMKIIβ is predominant as compared to CaMKIIα, almost no difference in activity was found among the wild-type mouse, heterozygous mouse, and homozygous mouse as shown in FIG. 8. Accordingly, the CaMKIIα in which the point mutation has been introduced into the gene is considered to be of an inactive type having no protein kinase activity.

From the results described above, in the inactive CaMKIIα knockin mouse, the expression of CaMKIIα protein is maintained almost normally but its protein kinase activity alone is impaired.

Example 6

Birthrate and Survival Rate of Inactive CaMKIIα Knockin Mouse

The genotype and sex ratios of 93 mice that were born by mating heterozygous mice were analyzed 4 weeks after their birth. The results are shown in Table 1 below.

TABLE 1

|  | homo | hetero | wild | total |
|---|---|---|---|---|
| male | 9 (20.5%) | 26 (59.1%) | 9 (20.5%) | 44 [47.3%] |
| female | 10 (20.4%) | 24 (49.0%) | 15 (30.6%) | 49 [52.7%] |
| total | 19 (20.4%) | 50 (53.8%) | 24 (25.8%) | 93 [100%] |

As shown in Table 1, it turned out that they were born in a Mendelian fashion, specifically, approximately half the total was heterozygous mice while the wild-type and homozygous mice each accounted for approximately one-fourth of the total. That is, it was proved that the gene mutation itself introduced into a mouse genome has no direct effect on the birth and survival of animals. Moreover, the ratios of male and female were approximately identical to each other. Knockout mice often have considerably reduced reproduction power, but such reduction in reproduction power is not found in the inactive CaMKIIα knockin mouse of the present invention. From this point of view, the inactive CaMKIIα knockin mouse of the present invention can be said to be a highly useful mouse.

Example 7

Decrease in Neuronal Activity of Inactive CaMKIIα Knockin Mouse

Figure 9:
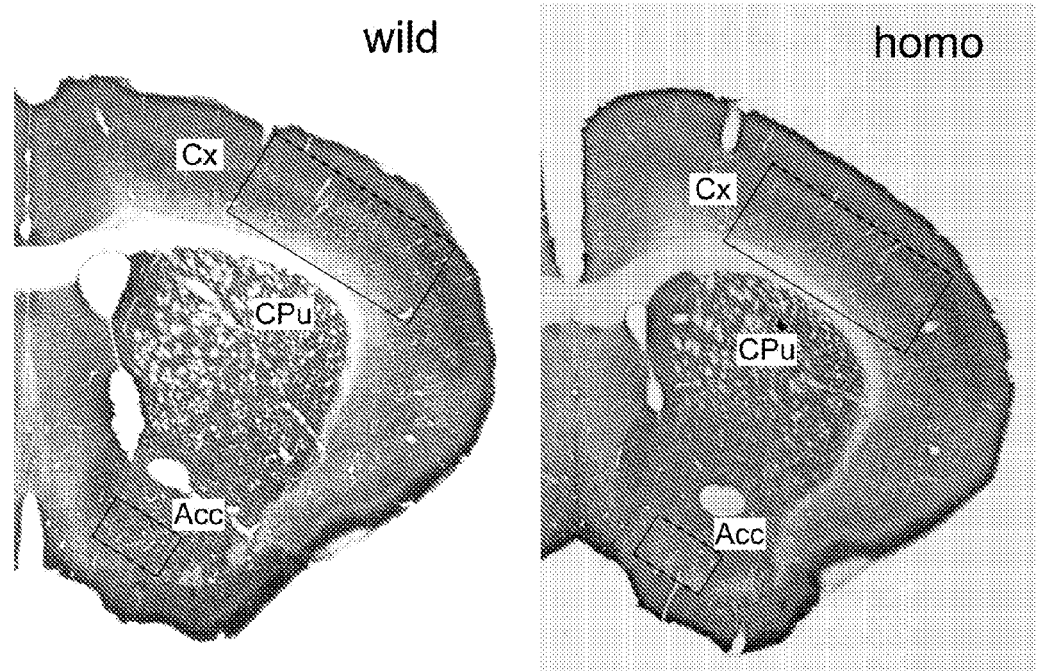
FIG. 9 shows the results of cytochrome oxidase activity staining of mouse brains. The left panel shows a brain section of a wild type while the right panel shows that of a homozygous mouse (homo) that is the inactive CaMKIIα knockin mouse of one example of the present invention.

By cytochrome oxidase activity staining that reflects the neuronal activity, it was examined whether there were any differences in neuronal activity between the wild-type mouse and the inactive CaMKIIα knockin mouse. FIG. 9 shows the resultant brain sections, where the left panel shows the brain section of the wild-type mouse while the right panel shows the brain section of the homozygous mouse (homo) that is the inactive CaMKIIα knockin mouse of the present example.

As shown in FIG. 9, no significant difference in activities in the cerebral cortex (Cx) and corpus striatum (CPu) was found between the wild-type mouse and the homozygous mouse. However, the homozygous mouse had lower activity in the nucleus accumbens (Acc) as compared to the wild-type mouse. In order to make a quantitative comparison, an average concentration in the region surrounded by the rectangle was determined with respect to each of the sections. When comparing the ratio (Acc/Cx) of the value in the nucleus accumbens to the value in the cerebral cortex, the ratio was 120.1% in the wild-type mouse while being 99.8% in the homozygous mouse. The homozygous mouse had a lower cytochrome oxidase activity in the nucleus accumbens. This result shows a decrease in neuronal activity in the nucleus accumbens of the homozygous mouse.

Example 8

Decrease in Convulsive Threshold and Mortality in Inactive CaMKIIα Knockin Mouse Convulsion inducing agent, pentylenetetrazole, was intraperitoneally injected (50 mg/kg) into adult mice. As a result, generalized clonus was found in the wild-type mouse but did not develop into convulsion. On the other hand, the homozygous mouse, being an inactive CaMKIIα knockin mouse of the present invention, had generalized clonus followed by clonic and tonic convulsion. Furthermore, some of them died subsequently. Thus, more serious convulsion was observed in the homozygous mouse. Accordingly, the inactive CaMKIIα knockin mouse is considered to have a decreased convulsive threshold as compared to a wild type animal.

In addition, we examined the number of mice that died during the period between 4 weeks and half a year after birth. The number of the wild-type mice that died was 0 out of 53 (0%) while those of the heterozygous mice and the homozygous mice that died were 5 out of 95 (5%) and 12 out of 48 (25%), respectively. The inactive CaMKIIα knockin mice had a clearly higher mortality. This result is considered to reflect that the inactive CaMKIIα knockin mice are vulnerable to external and internal invasion.

The above-mentioned results indicate the possibility that the inactive CaMKIIα knockin animal of the present invention is useful as a model animal of epileptic seizure and brain disorders.

INDUSTRIAL APPLICABILITY

In the inactive CaMKIIα knockin animal and knockin cell of the present invention, the protein kinase activity alone of CaMKIIα has been impaired. Accordingly, the present invention is widely usable, as a specific loss-of-functional animal (or cell), for various studies of brain and neuroscience including studies of learning disability, dysmnesia, epileptic seizure and brain disorders.

The invention claimed is:

1. An inactive $Ca^{2+}$/calmodulin-dependent protein kinase IIα (CaMKIIα) knockin nonhuman animal, wherein a CaMKIIα gene of one or both of homologous chromosomes is substituted into an inactive type so that an inactive CaMKIIα is expressed, wherein lysine corresponding to Lys-42 in the catalytic domain of mouse CaMKIIα is substituted by arginine; and thereby a protein kinase activity of CaMKIIα is specifically impaired while a calmodulin binding capacity of CaMKIIα and a capacity of multimerizing subunits are maintained, wherein the nucleus accumbens of the brain of the inactive CaMKIIα knockin nonhuman animal has lower neuronal activity as compared to that of a wild-type, while there is no substantial difference in neuronal activities in the cerebral cortex and caudate-putamen as compared to those of the wild-type, and wherein the inactive CaMKIIα knockin nonhuman animal is produced by a gene targeting method.

2. The inactive CaMKIIα knockin nonhuman animal of claim 1, wherein the inactive CaMKIIα knockin nonhuman animal is a rodent animal.

3. The inactive CaMKIIα knockin nonhuman animal of claim 2, wherein the inactive CaMKIIα knockin nonhuman animal is a mouse.

* * * * *